US010098439B2

(12) United States Patent
Zhu et al.

(10) Patent No.: US 10,098,439 B2
(45) Date of Patent: Oct. 16, 2018

(54) ONE-BELT HARNESS

(71) Applicant: Honeywell International Inc., Morristown, NJ (US)

(72) Inventors: Jacky Zhu, Shanghai (CN); Zhao Xia Jin, Shanghai (CN); Jimmy Zheng, Shanghai (CN); Bruce Liu, Shanghai (CN); Ning Qin, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 919 days.

(21) Appl. No.: 14/225,173

(22) Filed: Mar. 25, 2014

(65) Prior Publication Data

US 2014/0305437 A1    Oct. 16, 2014

Related U.S. Application Data

(60) Provisional application No. 61/812,677, filed on Apr. 16, 2013.

(51) Int. Cl.
  *A45F 3/02* (2006.01)
  *A62B 25/00* (2006.01)
  (Continued)

(52) U.S. Cl.
  CPC ............... *A45F 3/02* (2013.01); *A62B 25/00* (2013.01); *A41D 2400/48* (2013.01);
  (Continued)

(58) Field of Classification Search
  CPC .............. A45F 3/02; A45F 2003/025; A45F 2003/146; A62B 25/00; A41D 2400/48;
  (Continued)

(56) References Cited

U.S. PATENT DOCUMENTS 3,583,761 A * 6/1971 Hume ................. B60N 2/2821
                                                    297/253
3,797,715 A * 3/1974 Scialdone ................. A45F 3/14
                                                    224/587
(Continued)

FOREIGN PATENT DOCUMENTS

WO    WO2012061806 A1    5/2012

OTHER PUBLICATIONS

Steinhoff, P. Equipment How-To's, Doing It Right [Online]. Jan. 2014 [retrieved on Jan. 28, 2014]. Retrieved from <http://dir-diver.com/en/equipment/backplate_adjustment.html>.

*Primary Examiner* — Timothy Stanis
(74) *Attorney, Agent, or Firm* — Craige Thompson; Thompson Patent Law

(57) ABSTRACT

Apparatus and associated methods relate to a body-worn unitary harness having a shoulder portion and a waist portion in tensile communication with one another, such that both the shoulder and the waist portions can be simultaneously adjusted using a single adjustment mechanism to conform to a wearer's body. In an illustrative embodiment, a length of webbing may thread through an angle-turning buckle and change direction therein. Tensile forces in the length of webbing may be directed in different directions on either side of the angle-turning buckle. A single clasp may facilitate both donning and doffing of the unitary harness. An implement connector may be coupled to a hip member and configured to connect an implement to the unitary harness. Various exemplary unitary harnesses may provide comfortable implement carrying capacity while automatically adjusting relative waist and shoulder lengths to accommodate a user's movements and positions.

13 Claims, 6 Drawing Sheets

(51) Int. Cl.
*A61M 16/06* (2006.01)
*A45F 3/14* (2006.01)

(52) U.S. Cl.
CPC ... *A45F 2003/025* (2013.01); *A45F 2003/146* (2013.01); *A61M 16/0672* (2014.02)

(58) Field of Classification Search
CPC ..... A41D 2400/482; A61F 5/37; A61F 5/373; A61F 5/3746; A61F 5/3738; A61F 5/3761
USPC ............................. 2/300, 311, 312, 320, 460
See application file for complete search history.

(56) References Cited

U.S. PATENT DOCUMENTS

| | | | | |
|---|---|---|---|---|
| 4,685,456 | A * | 8/1987 | Smart | A61M 16/08 128/204.18 |
| 4,739,913 | A * | 4/1988 | Moore | A62B 9/04 128/205.22 |
| 4,979,659 | A * | 12/1990 | Boyd | A62B 9/04 128/205.22 |
| 5,806,741 | A | 9/1998 | Kirk | |
| 6,155,471 | A * | 12/2000 | Lichtenberger | B25H 3/006 224/242 |
| 6,443,347 | B1 | 9/2002 | Elizalde et al. | |
| 7,726,312 | B2 * | 6/2010 | Chapman | A45F 3/14 128/200.24 |
| 2012/0103724 | A1 * | 5/2012 | Reynolds | A62B 35/0018 182/3 |

* cited by examiner

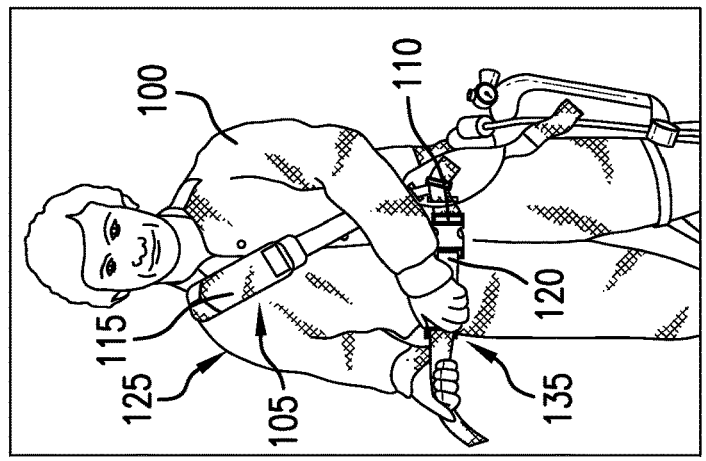
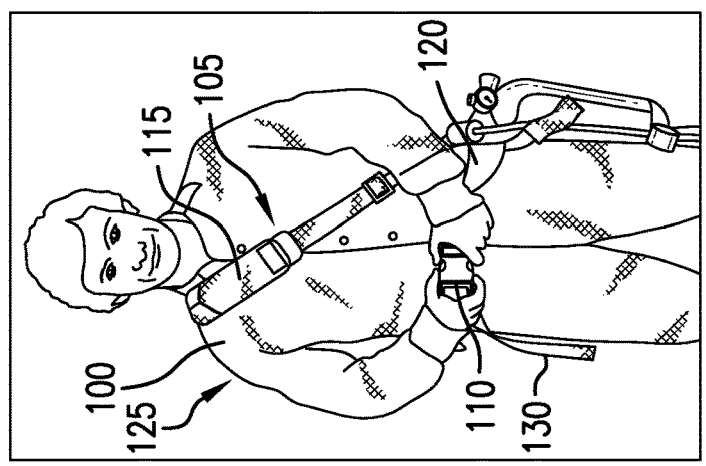
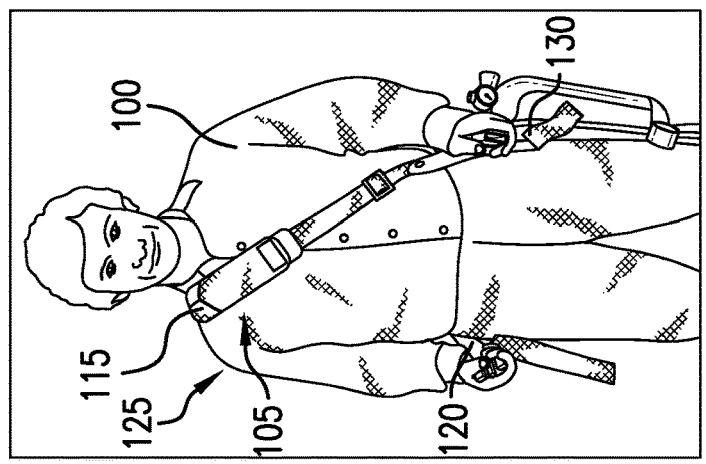

ONE-BELT HARNESS

CROSS-REFERENCE TO RELATED APPLICATIONS

This application claims priority to the following U.S. Patent application(s), the entire disclosure of each of which is incorporated herein by reference:
61/812,677 One-Belt Harness Apr. 16, 2013.

TECHNICAL FIELD

Various embodiments relate generally to harnesses having two or more body-circling loops in tensile communication with one another.

BACKGROUND

Webbed harnesses are worn by users for a variety of reasons. Webbed harnesses may be used in fall-protection systems to secure a user to a rigid structure. Such harnesses may have a lanyard connection point to attach a lanyard or lifeline to the harness. The lanyard or lifeline may attach at a second end to a rigid structure, which may secure the user to that structure. Webbed harnesses may be used as child restraint devices. Some parents may tether themselves to their child using a webbed harness. Such a configuration may restrict the distance from a parent that a child may roam.

SUMMARY

Apparatus and associated methods relate to a body-worn unitary harness having a shoulder portion and a waist portion in tensile communication with one another, such that both the shoulder and the waist portions can be simultaneously adjusted using a single adjustment mechanism to conform to a wearer's body. In an illustrative embodiment, a length of webbing may thread through an angle-turning buckle and change direction therein. Tensile forces in the length of webbing may be directed in different directions on either side of the angle-turning buckle. A single clasp may facilitate both donning and doffing of the unitary harness. An implement connector may be coupled to a hip member and configured to connect an implement to the unitary harness. Various exemplary unitary harnesses may provide comfortable implement carrying capacity while automatically adjusting relative waist and shoulder lengths to accommodate a user's movements and positions.

Various embodiments may achieve one or more advantages. For example, some embodiments may be donned and doffed easily and/or quickly using a single clasp member. Opening the clasp member may remove the tension of the webbing throughout the entire harness facilitating easy removal. Donning the harness may be performed by securing a single clasp after proper positioning. In some embodiments, the harness may be fit to a wearer by operating a single adjustment mechanism. The single adjustment mechanism may provide a uniform tension throughout the webbing. For example, a waist loop and a shoulder loop may be simultaneously tightened to fit a wearer by operation of a single adjustment mechanism. In some embodiments, the harness may have been previously adjusted to fit a certain wearer, and the harness may properly fit the wearer by simply securing the clasp. In an exemplary embodiment, a load on the shoulder may continuously be distributed to a load on the waist as the wearer shifts position, for example.

The details of various embodiments are set forth in the accompanying drawings and the description below. Other features and advantages will be apparent from the description and drawings, and from the claims.

BRIEF DESCRIPTION OF THE DRAWINGS

FIGS. 1A-1C depict the donning of an exemplary One-Belt Harness.

Like reference symbols in the various drawings indicate like elements.

DETAILED DESCRIPTION OF ILLUSTRATIVE EMBODIMENTS

Figure 2:
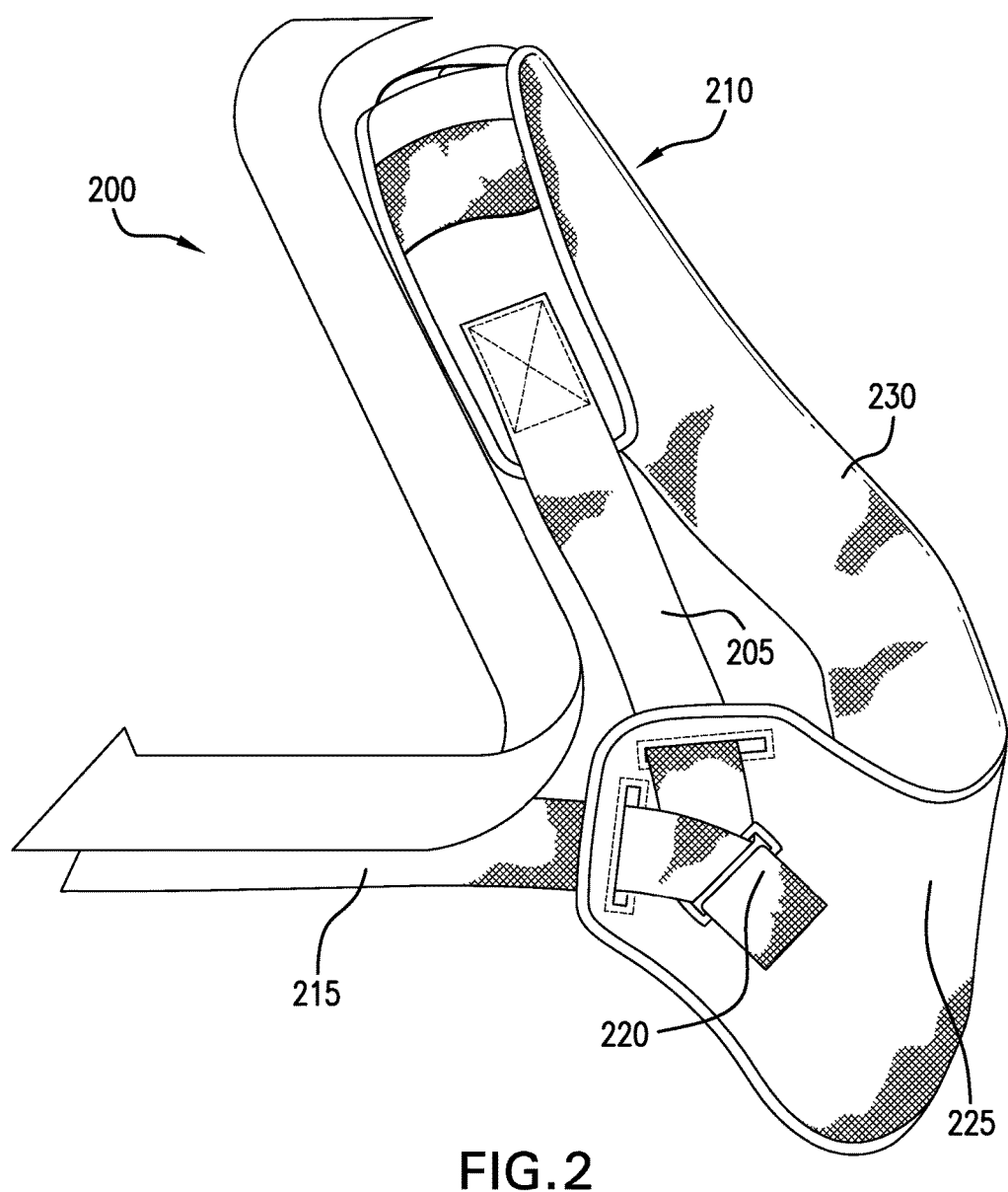
FIG. 2 depicts a close-up diagram of an exemplary One-Belt Harness showing an example angle-turning buckle.

To aid understanding, this document is organized as follows. First, an exemplary donning of an exemplary One-Belt Harness (OBH) will be described, with reference to FIGS. 1A-1C. Then exemplary securing operations of the OBH will be described, with reference to FIG. 2. An exemplary implement attachment device will be disclosed, with reference to FIG. 3. Exemplary OBH configured to carry an exemplary Pressure-Demand Air Respirator (PDAR) will be described with reference to FIGS. 4 and 5. Finally, an alternate embodiment of an OBH having two shoulder loops will be disclosed with reference to FIG. 6.

FIGS. 1A-1C depict the donning of an exemplary One-Belt Harness (OBH). In these exemplary figures, three phases of a wearer 100 donning an exemplary OBH 105 are depicted. The OBH 105 has webbing 110 that includes a shoulder loop 115 in tensile communication with a waist loop 120. In the FIG. 1A depiction, the wearer 100 has positioned the shoulder loop 115 over a shoulder 125 of the wearer 100, but has yet to secure or tighten the OBH 105 to the wearer 100. In FIG. 1B, the wearer 100 is securing the OBH 105 to the wearer 100 using a waist located securing member 130. In FIG. 1C, the wearer 100 is adjusting the tension of the OBH 105 using an adjustment mechanism 135 located on the waist portion of the OBH 105. The adjustment mechanism 135 may adjust the length of the combined shoulder loop 115 and waist loop 120. If, for example, the wearer 100 adjusts the tension of the OBH 105 using the adjustment member 130, the waist loop 120 may be reduced. As the waist loop is reduced, tension in the waist loop 120 may be translated to tension in the shoulder loop 115, for example. In this way, as the wearer 100 adjusts the tension of the webbing 110 via the adjustment mechanism 135, both the waist loop 120 and the shoulder loop 115 may be securely fit to the wearer 100. The OBH 105 may advantageously be donned and properly secured to both a waist and a shoulder using a single securing member 130 and a single adjustment mechanism 135.

In the depicted embodiment, the adjustment mechanism 135 is attached to the securing device 130. Doffing the exemplary OBH 105 may be performed similarly to the donning operation described above, but in reverse order of operation, for example. The wearer 100, having adjusted the OBH 105 to fit the wearer 100 may not need to adjust the tension, in some embodiments. For example, when doffing a fit OBH 105, the wearer 100 may simply unsecure the OBH 100 using the securing member 130. The wearer may then remove the shoulder loop 115 from the wearer's shoulder 125 and stow the OBH 105. The OBH 105 may then remain adjusted for proper fit of the wearer 100 when next used, for example. By unsecuring the OBH, the tension of the waist loop 120 may be released. The released waist loop tension may release the tension of the shoulder loop 115. In this way, the adjustment mechanism 135 may not be required to release the tension of the webbing 110, for example.

FIG. 2 depicts a close-up diagram of an exemplary One-Belt Harness showing an example angle-turning buckle. In this figure, an exemplary One-Belt Harness (OBH) 200 is depicted. The depicted OBH 200 has a single belt 205 that has a shoulder portion 210 and a waist portion 215. A point of delineation between the shoulder portion 210 and the waist portion 115 occurs substantially at an angle-turning buckle 220. The angle-turning buckle 220 serves as a pulley to transfer the movements from waist portion 215 to shoulder portion 210, and allow the tension of the belt 205 to be uniform in both the shoulder portion 210 and the waist portion 215. When one tightens the waist portion 215, tension of the waist portion 215 may increase. The waist portion 215 may be in tensile communication with the shoulder portion 210. Thus, the tension of the shoulder portion 210 may increase in response to the increased tension of the waist portion 210. The tension of the shoulder portion 210 may increase until the tension of the waist portion 215 and the shoulder portion 210 are substantially equal, for example. Accordingly, the full harness 200 may uniformly be tightened to fit to a human body.

Also depicted in FIG. 2 is a webbing configuration hub 225, to which the belt 205 is coupled. The exemplary webbing configuration hub 225 may present a soft surface 230 which may provide comfort to a wearer of the OBH 200. In various embodiments the belt 205 may be rigidly attached at some point to the webbing configuration hub 225. In some embodiments the belt 205 may be releasably attached to the webbing configuration hub 225. In an exemplary embodiment, the belt 205 may freely travel along and perhaps through portions of the webbing configuration hub 225. In an exemplary embodiment the webbing configuration hub 225 has a first aperture and a second aperture through which the belt 205 is configured to travel.

Figure 3:
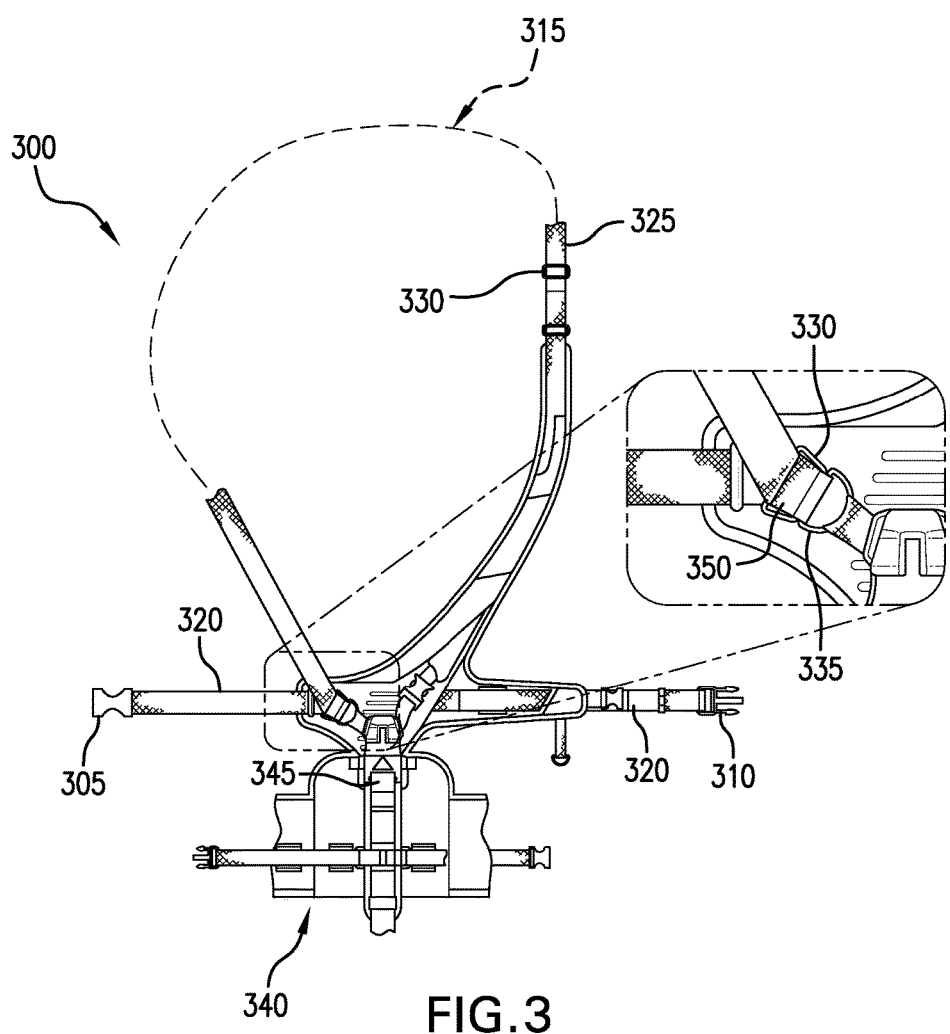
FIG. 3 depicts an exemplary One-Belt Harness opened so as to display various components.

FIG. 3 depicts an exemplary One-Belt Harness opened so as to display various components. In FIG. 3, a plan view of an exemplary OBH 300 in an open position is shown. In this depiction, a clasp 305, 310 includes a female member 305 and a male member 310. A webbing 315 includes a waist portion 320 and a shoulder portion 325. The waist portion 320 and the shoulder portion 325 are connected via an angle-turning buckle 330. In this embodiment, the clasp 305, 310 is installed on the waist portion 320 of the webbing 315. In this embodiment, the angle-turning buckle 330 may transfer the fastening or loosening effects between the waist portion 320 and the shoulder portion 325 and may substantially equalize the tension of the waist portion 320 and the shoulder portion 325. A single clasp 305, 310 may permit the wearer to open the waist portion 320 of the belt while simultaneously loosening the shoulder portion 325 of the belt in a doffing operation. In various embodiments, the clasp 305, 310 may be coupled to the webbing 315 at various locations along the webbing 315. For example, a clasp 305, 310 may be including in a waist portion 320. In some examples, a clasp 305, 310 may be coupled to a shoulder portion 325. In some embodiments, clasps may be coupled to both a shoulder portion 325 and a waist portion 320. Certain embodiments may further provide a second clasp located in another location of the belt. In such embodiments, the user may doff the belt using either of the two clasps to open and loosen the OBH 300. Various types of clasps may be used in various embodiments. For example, a belt buckle type of clasp may be used. In some embodiments, the webbing 315 may be secured by tying two ends of the webbing 315 together.

In various examples, the OBH 300 may dynamically adjust the length of the waist and shoulder portions 320, 325 in response to body movements of the wearer. For example, as the wearer moves from an erect-standing position to a bent-at-the-waist position, the OBH 300 may dynamically and reciprocally adjust the length of the waist portion 320 and the shoulder portion 325. In some embodiments, the dynamic and reciprocal reallocation may advantageously substantially reduce excess slack in one of the portions 320, 325 while simultaneously accommodating extra length in the other portion 325, 320, respectively, to avoid restricting user movement.

FIG. 3 also depicts an exemplary adjustment mechanism 330. The depicted adjustment mechanism 330 in this embodiment is located on the shoulder portion 325 of the belt. The adjustment mechanism 330 may be located at any location of the webbing 315. This adjustment mechanism 330 may advantageously provide for more or less length to the webbing 315 to accommodate various size wearers, for example. In some embodiments, an adjustment mechanism 330 may be coupled to a clasp member (e.g. 305 and/or 310). In some embodiments more than one adjustment mechanism 330 may be used. In such embodiments, a wearer may be able to adjust the webbing 315 using an adjustment mechanism that is most convenient to the wearer, for example. Because the waist portion 320 and the shoulder portion 325 may be in tensile communication with each other, any adjustment that changes the tension of one portion 320, 325 may simultaneously adjust the tension in the other portion 325, 320, respectively. In response to changes in the combined length of the shoulder portion 325 and waist portion 320 using any of the adjustment mechanisms, both the length of the waist portion 320 and the length of the shoulder portion 325 may simultaneously adjust.

The angle-turning buckle 330 depicted in this figure has a pivotable bracket 335. This pivotable bracket may permit the angle of the angle-turning buckle 330 to accommodate differently shaped wearers. The depicted angle-turning buckle 330 may have a webbing aperture 350, through which the webbing 315 may travel. The webbing aperture may have a major dimension sized to receive a webbing 315 having up to a predetermined width. The webbing aperture 350 may have a minor dimension sized to receive a webbing's thickness such that a length of webbing is slidable through the angle-turning buckle. The angle-turning buckle may act like a webbing reflector, reflecting the direction of the webbing about a normal vector to a reflection line, for example. The normal direction may be in a direction of the minor axis of the webbing aperture 350 for example. The direction of a length of waist portion webbing immediately adjacent to the webbing aperture 350 may have an "angle of incidence" with respect to the normal direction. The direction of a length of shoulder portion webbing immediately adjacent to the webbing aperture 350 may have an "angle or reflection" with respect the normal direction that is approximately equal to the "angle of incidence." This reflection metaphor describes the relationship of the angles of the webbing lengths near the webbing aperture 350. The metaphor fails in that neither length of webbing (the waist portion length and the shoulder portion length) is incident and neither is reflected. But the similar angel relationship would describe the relationship between the lengths if one of the lengths were an incident beam and the other were a reflected beam, in this example.

This example of an OBH 300 is also shown to be connected to load module 340. The load module 340 is connected to the OBH via a load connector 345. Various different types of load modules 340 may be accommodated by such a load connector 345.

Figure 4:
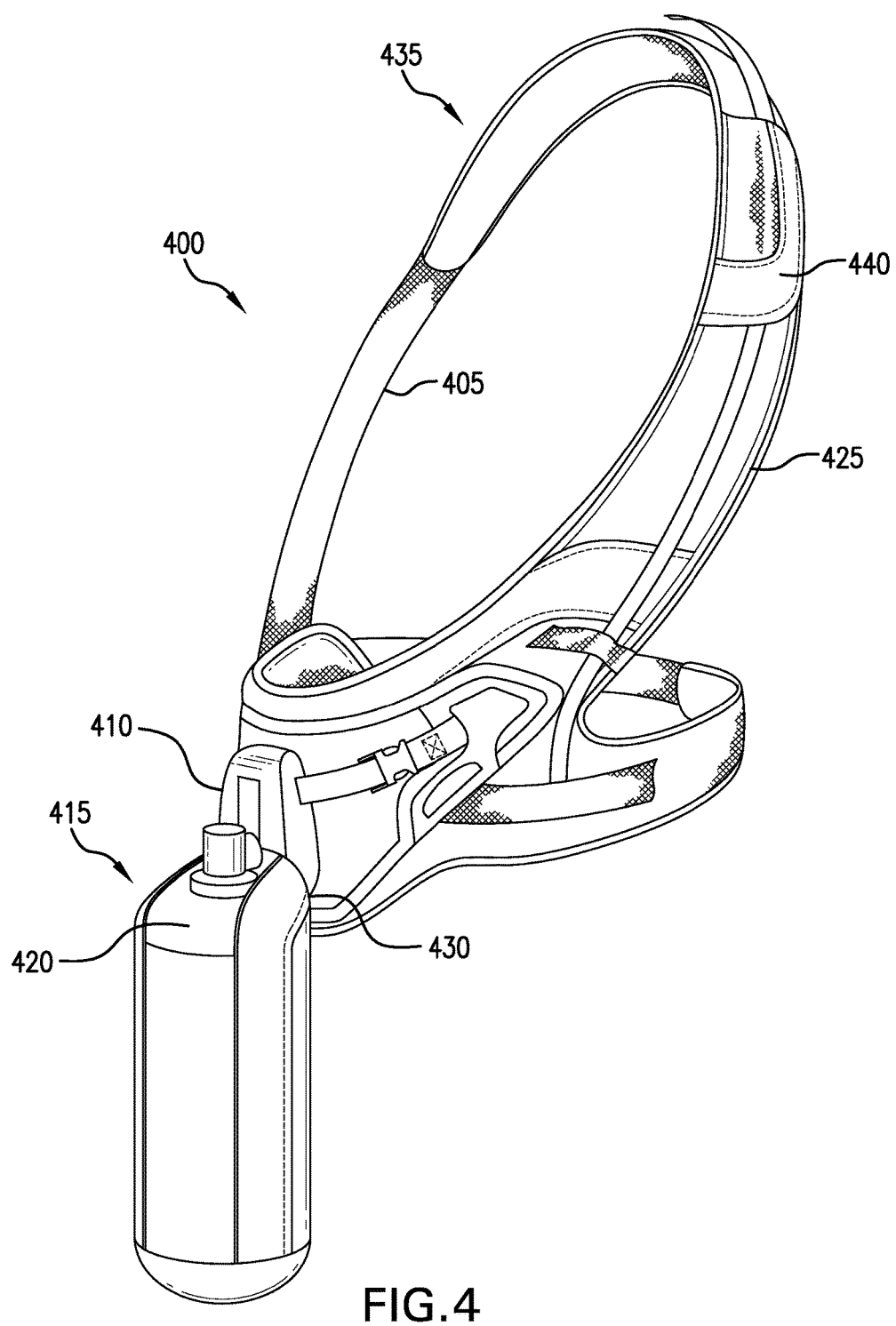
FIG. 4 depicts an exemplary Pressure-Demand Air Respirator (PDAR) carrying device with integral breathing tube.

FIG. 4 depicts an exemplary Pressure-Demand Air Respirator (PDAR) carrying device with integral breathing tube. In the depicted embodiment, an exemplary PDAR carrying device 400 includes a one-belt webbing 405 and a cylinder capture member 410. The exemplary cylinder capture member 410 has a pocket 415 sized to receive a breathing gas cylinder 420. The PDAR carrying device 400 has a gas-connecting tube 425 having a cylinder connecting end 430 and a mask connecting end 435. The cylinder connecting end is shown to be connected to the breathing gas cylinder 420. The mask connecting end is configured to attach to a breathing mask to be worn on the face of a wearer. The gas-connecting tube runs along the shoulder loop of the PDAR carrying device 400. In the depicted embodiment, the gas-connecting tube is captured or surrounded by material loops 440. In some embodiments, the gas-connecting tube may be captured within the PDAR carrying device 400 along a length of the webbing 405.

Figure 5:
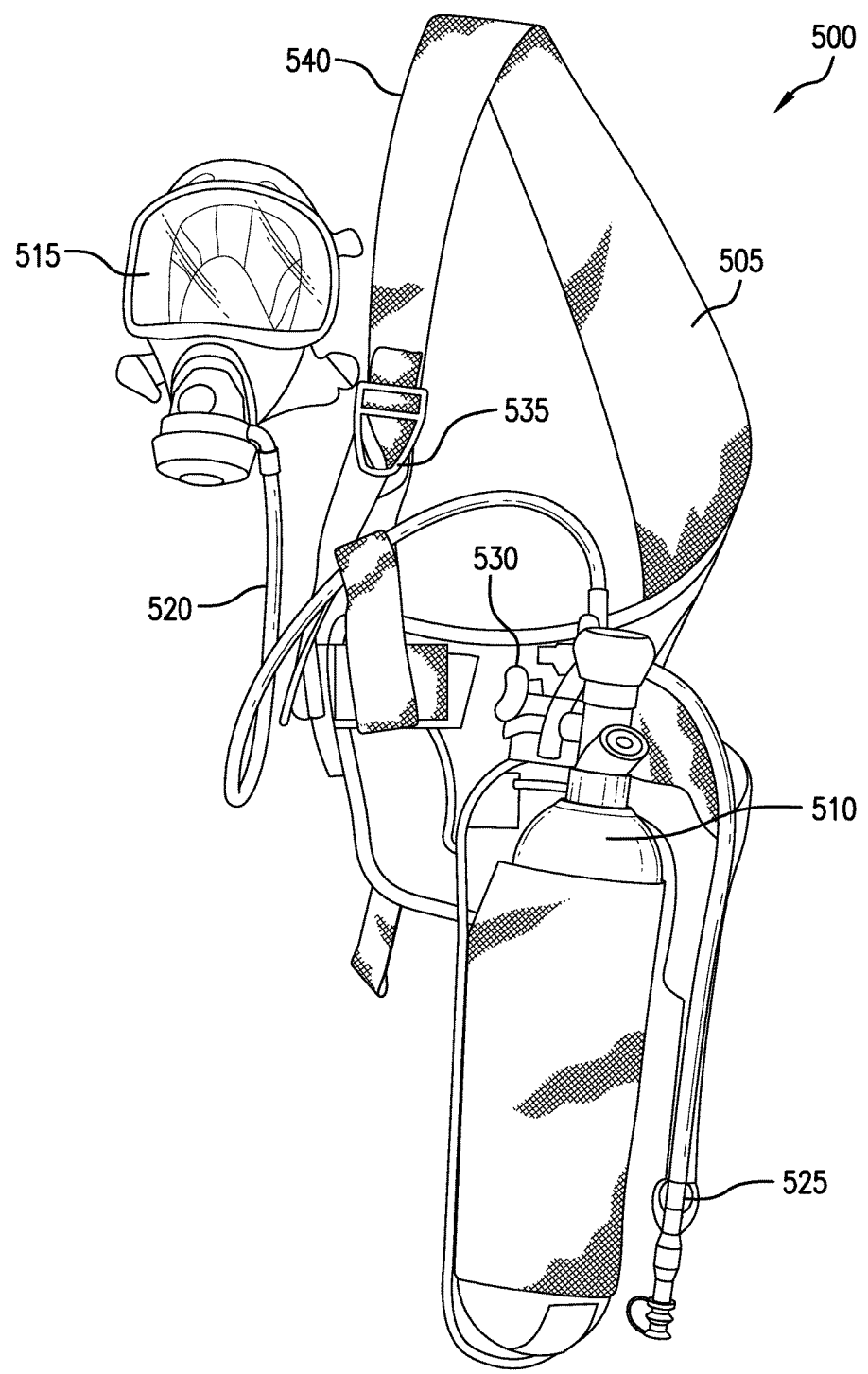
FIG. 5 depicts an exemplary Pressure-Demand Air Respirator (PDAR) system with breathing mask.

FIG. 5 depicts an exemplary Pressure-Demand Air Respirator (PDAR) system with breathing mask. In the FIG. 5 depiction, an exemplary PDAR system 500 includes a One-Belt Harness (OBH) 505 coupled to a breathable-gas cylinder 510. A breathing mask 515 is connected to the breathable-gas cylinder 510 via an air hose 520. The breathable-gas cylinder 510 may be a back-up source of breathable air for the user. In the depicted embodiment, a house-gas connecting line 525 may be used to connect the PDAR system to house air. A selection switch 530 may be used to select between the house gas and the breathable-gas cylinder 510, for example. An adjustment mechanism 535 for the tightening/loosening of the OBH 505 is on a shoulder loop section 540 of the OBH 505.

Figure 6:
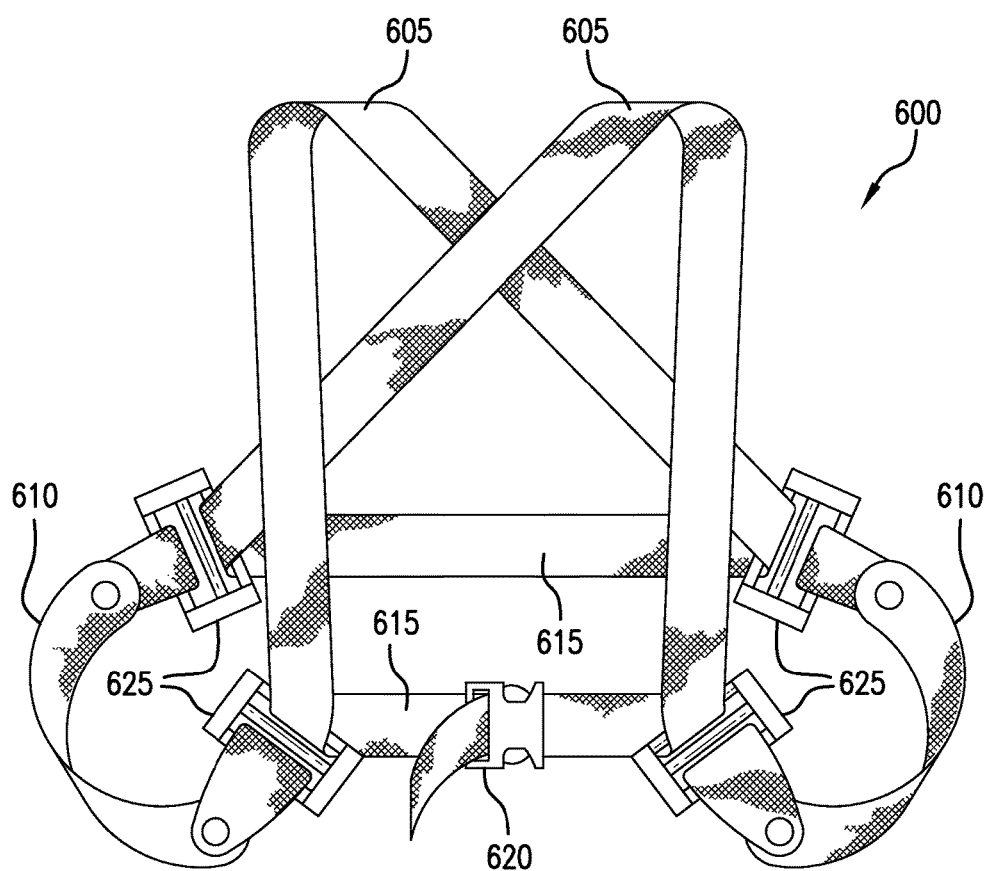
FIG. 6 depicts an exemplary one-belt harness having two shoulder straps.

FIG. 6 depicts an exemplary One-Belt Harness having two shoulder straps. In the FIG. 6 embodiment, an exemplary One-Belt Harness (OBH) 600 includes two shoulder loop sections 605. In the depicted embodiment, the waist loop includes two fixed-size sections 610 and two adjustably-sized sections 615. In the depicted embodiment, a webbing includes both the adjustably-sized waist sections 615 as well as the two shoulder loop sections 605. Each of the webbing sections is in tensile communication with all other webbing sections. For example, if a tightening mechanism 620 is used to decrease the combined length of a body-securing portion of the webbing 605, both adjustably-sized waist sections 615 and both shoulder loop sections 605 may be decreased in length, for example. In some embodiments, a dorsal member may help maintain a crossing location of the shoulder loops at a dorsal region of the back, for example. In the depicted embodiment, four webbing redirection members 625 provide webbing tension to be directed along the webbing sections. In some embodiments, the webbing redirection members may be doubly slotted members, such as those depicted in FIG. 6. In some embodiments, pulley-type redirection member. In such a member, a rotatable wheel may facilitate the tensile coupling between adjacent lengths on either side of the redirection member, for example. In some embodiments, a fixed circular wheel may provide a redirection path for the webbing.

Although various embodiments have been described with reference to the Figures, other embodiments are possible. For example, the belt of an exemplary OBH may travel through portions of the harness, but may be unconnected from it. In such an example, a single clasp and a single adjustment mechanism may be able to be located wherever the user desires. Thus the clasp may be located on the shoulder portion or the waist portion. In various embodiments, the shoulder portion of the belt may be connected to the waist portion of the belt via two angle-turning buckles, one on either side of the waist. In some embodiments, only one angle-turning buckle may be used. In such embodiments, the waist portion and the shoulder portion may be affixed to the harness on the side without an angle-turning buckle.

In an exemplary embodiment, a load module may be adapted to hold a pressure-demand air respirator. In accordance with another embodiment, the load module may be adapted to hold various tools. Some embodiments may include a gun holster. For example, police officers may wear such OBHs under their uniform. In some embodiments, a backpack may include an OBH attached to a payload carrying bag. In some embodiments, a fall-protection harness may be securable using one-belt tightening techniques.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. A Pressure-Demand Air Respirator (PDAR) carrying device to be worn by a user, the device comprising:
    a webbing-configuration hub comprising a first aperture and a second aperture;
    a direction-changing buckle rotatably connected to the webbing-configuration hub, the direction-changing buckle having a webbing aperture having a major dimension sized to receive a webbing having up to a predetermined width and having a minor dimension sized to receive a webbing's thickness such that a portion of webbing is slidable through the direction-changing buckle;
    a breathable-gas cylinder pocket to releasably receive an air cylinder;
    a webbing configured to be worn by a wearer, the webbing comprising a shoulder-loop section in a tension relationship with a waist-loop section, wherein a tension in one of the shoulder-loop and waist-loop sections is transmitted to the other of the waist-loop and shoulder-loop sections, respectively, at the direction-changing buckle's webbing aperture through which the webbing threads, wherein, when worn, the webbing is configured to travel a path:
        a) from a back-left waist location;
        b) along the waist along the back, around the right side and along the front;
        c) through the first aperture of the webbing-configuration hub;

d) through the direction-changing buckle at a front-left waist location;
e) through the second aperture of the webbing-configuration hub;
f) up and across the front torso and over the right shoulder; and,
g) down and across the back to a back-left waist location;

a hand-operated clasp coupled to the webbing and configured to open and/or securely close the webbing about a body of the wearer; and, only one hand-operated tightening mechanism coupled to the webbing to provide combined length adjustment of the shoulder-loop and waist-loop sections, the hand-operated tightening mechanism being located on an anterior portion of the shoulder-loop section when worn by the wearer, wherein, when worn by the wearer with the hand-operated clasp securely closed, the direction-changing buckle rotates in response to adjusting the webbing by the hand-operated tightening mechanism to fit the wearer such that a direction of the minor dimension of the webbing aperture approximately bisects an angle between a waist-loop segment of webbing immediately adjacent to the webbing aperture and a shoulder-loop segment of webbing immediately adjacent to the webbing aperture.

2. The device of claim 1, wherein a length of the shoulder-loop section reduces in response to enlarging a length of the waist-loop section, and the length of the waist-loop section reduces in response to enlarging the length of the shoulder-loop section, when the hand-operated clasp is securely closed and without adjusting the hand-operated tightening mechanism.

3. The device of claim 1, further comprising a breathing tube extending from a cylinder region near an implement connecting member to a mask region, the breathing tube travels along a portion of the shoulder loop section of the webbing.

4. The device of claim 3, further comprising a breathing mask, coupled to that breathing tube at the mask region.

5. An implement carrying device to be worn by a user, the device comprising:
a webbing-configuration hub comprising a first aperture and a second aperture;
a direction-changing buckle connected to the webbing-configuration hub, the direction-changing buckle having a webbing aperture having a major dimension sized to receive a webbing having up to a predetermined width and having a minor dimension sized to receive a webbing's thickness such that a portion of webbing is slidable through the direction-changing buckle;
an implement connecting member coupled to the webbing-configuration hub and configured to releasably connect to an implement;
a webbing configured to be worn by a wearer, the webbing comprising a shoulder-loop section in a tension relationship with a waist-loop section, wherein a tension in one of the shoulder-loop and waist-loop sections is transmitted to the other of the waist-loop and shoulder-loop sections, respectively, at the direction-changing buckle's webbing aperture through which the webbing threads, wherein, when worn, the webbing is configured to travel a path:
a) from a back-left waist location;
b) along the waist along the back, around the right side and along the front;
c) through the first aperture of the webbing-configuration hub;
d) through the direction-changing buckle at a front-left waist location;
e) through the second aperture of the webbing-configuration hub;
f) up and across the front torso and over the right shoulder; and,
g) down and across the back to a back-left waist location;

a hand-operated clasp coupled to the webbing and configured to open and/or securely close the webbing about a body of the wearer; and, only one hand-operated tightening mechanism coupled to the webbing to provide combined length adjustment of the waist-loop and the shoulder-loop sections, the hand-operated tightening mechanism being located on an anterior portion of the shoulder-loop section when worn by the wearer.

6. The device of claim 5, wherein a length of the shoulder-loop section reduces in response to enlarging a length of the waist-loop section, and the length of the waist-loop section reduces in response to enlarging the length of the shoulder-loop section, when the hand-operated clasp is securely closed and without adjusting the hand-operated tightening mechanism.

7. The device of claim 5, wherein the implement connecting member is configured to hold a breathable-gas cylinder.

8. The device of claim 7, further comprising a securing member configured to secure the breathable-gas cylinder to the implement connecting member.

9. The device of claim 7, further comprising a breathing tube extending from a cylinder region near the implement connecting member to a mask region, the breathing tube travels along a portion of the shoulder loop section of the webbing.

10. The device of claim 9, further comprising a breathing mask, coupled to that breathing tube at the mask region.

11. An implement carrying device to be worn by a user, the device comprising:
a webbing-configuration hub comprising a first aperture and a second aperture;
means for changing a direction of a webbing where a waist loop transitions to a shoulder loop;
an implement connecting member coupled to the webbing-configuration hub and configured to releasably connect to an implement;
a webbing configured to be worn by a wearer, the webbing comprising a shoulder-loop section in a tension relationship with a waist-loop section, wherein a tension in one of the shoulder-loop and waist-loop sections is transmitted to the other of the waist-loop and shoulder-loop sections, respectively, at an aperture in the direction changing means through which the webbing threads, wherein, when worn, the webbing is configured to travel a path:
a) from a back-left waist location;
b) along the waist along the back, around the right side and along the front;
c) through the first aperture of the webbing-configuration hub;
d) through the direction-changing buckle at a front-left waist location;
e) through the second aperture of the webbing-configuration hub;

f) up and across the front torso and over the right shoulder; and, g) down and across the back to a back-left waist location;

a hand-operated clasp coupled to the webbing and configured to open and/or securely close the webbing about a body of the wearer; and only one hand-operated tightening mechanism coupled to the webbing to provide combined length adjustment of the shoulder-loop and waist-loop sections, the hand-operated tightening mechanism being located on an anterior portion of the shoulder-loop section when worn by the wearer.

12. The device of claim 11, wherein when worn by the wearer with the hand-operated clasp securely closed and without adjusting the hand-operated tightening mechanism, expanding the shoulder loop section reduces the waist loop section or expanding the waist loop section reduces the shoulder loop section.

13. The device of claim 11, wherein the implement connecting member is configured to hold a breathable-gas cylinder.

* * * * *